United States Patent [19]

Manyik et al.

[11] Patent Number: 4,596,787

[45] Date of Patent: Jun. 24, 1986

[54] PROCESS FOR PREPARING A SUPPORTED CATALYST FOR THE OXYDEHYDROGENATION OF ETHANE TO ETHYLENE

[75] Inventors: Robert M. Manyik, St. Albans; James H. McCain, Charleston, both of W. Va.

[73] Assignee: Union Carbide Corporation, Danbury, Conn.

[21] Appl. No.: 721,893

[22] Filed: Apr. 11, 1985

[51] Int. Cl.$^4$ .......................... B01J 23/18; B01J 23/20; B01J 23/22; B01J 23/28
[52] U.S. Cl. .................................... 502/312; 502/215; 502/303; 502/304; 502/306; 502/307; 502/309; 502/313; 502/315; 502/316; 585/658
[58] Field of Search ............... 502/215, 303, 304, 306, 502/307, 309, 312, 313, 315, 316; 585/658

[56] References Cited

U.S. PATENT DOCUMENTS 4,250,346  2/1981  Young et al. ...................... 585/658

OTHER PUBLICATIONS

The Oxidative Dehydrogenation of Ethane Over Catalyst Containing Mixed Oxide of Molybdenum and Vanadium: by E. M. Thorsteinson, T. P. Wilson, F. G. Young and P. H. Kasai, *Journal of Catalysis* 52, pp. 116–132 (1978).

*Primary Examiner*—W. J. Shine
*Attorney, Agent, or Firm*—George A. Skoler

[57] ABSTRACT

A process for low temperature oxydehydrogenation of ethane to ethylene uses an improved supported catalyst produced by impregnating the support with the soluble portion of a precursor catalyst solution and then activating the impregnated support. The activated impregnated support provides good selectivity to ethylene and avoids the problems which can arise from impregnation of the support with the soluble and insoluble portions of a precursor catalyst solution.

5 Claims, No Drawings

PROCESS FOR PREPARING A SUPPORTED CATALYST FOR THE OXYDEHYDROGENATION OF ETHANE TO ETHYLENE

FIELD OF THE INVENTION

The invention relates to a process for low temperature oxydehydrogenation of ethane to ethylene, and particularly to a process using an improved supported catalyst featuring good conversion and good selectivity.

BACKGROUND OF THE INVENTION

Low temperature oxydehydrogenation of ethane to ethylene has become well known since the publication of "The Oxidative Dehydrogenation of Ethane over Catalyst Containing Mixed Oxide of Molybdenum and Vanadium" by E. M. Thorsteinson, T. P. Wilson, F. G. Young and P. H. Kasai, *Journal of Catalysis* 52, pp. 116-132 (1978). This article discloses mixed oxide catalysts containing molybdenum and vanadium together with another transition metal oxide (Ti, Cr, Mn, Fe, Co, Ni, Nb, Ta, or Ce). The catalysts are active at temperatures as low as 200° C. for the oxydehydrogenation of ethane to ethylene.

The effectiveness of the oxydehydrogenation of ethane to ethylene is usually primarily determined by two parameters: conversion of ethane, and selectivity (efficiency) to ethylene. As used herein, these terms are defined as follows:

$$\text{conversion of ethane} = \frac{[CO]/2 + [CO_2]/2 + [C_2H_4]}{[CO]/2 + [CO_2]/2 + [C_2H_4] + [C_2H_6]}$$

$$\text{selectivity (efficiency) to ethylene} = \frac{[C_2H_4]}{[CO]/2 + [CO_2]/2 + [C_2H_4]}$$

wherein: [ ]=relative moles of the component and the production of acetic acid is negligible. The terms in the art are sometimes calculated differently but the values calculated either way are substantially the same.

Under certain reaction conditions, substantial amounts of acetic acid can be formed as a co-product and the effectiveness of the reaction to ethylene and acetic acid is calculated by the following equations:

conversion of ethane =

$$\frac{[CO]/2 + [CO_2]/2 + [C_2H_4] + [CH_3COOH]}{[CO]/2 + [CO_2]/2 + [C_2H_4] + [C_2H_6] + [CH_3COOH]}$$

selectivity (efficiency) to ethylene and acetic acid =

$$\frac{[C_2H_4] + [CH_3COOH]}{[CO]/2 + [CO_2]/2 + [C_2H_4] + [C_2H_6] + [CH_3COOH]}$$

U.S. Pat. No. 4,250,346 discloses catalytic oxydehydrogenation of ethane to ethylene at temperatures less than 550° C. in which the catalyst is a calcined composition comprising the elements Mo, X, and Y in the ratio $$Mo_a X_b Y_c$$

wherein:
X=Cr, Mn, Nb, Ta, Ti, V, and/or W
Y=Bi, Ce, Co, Cu, Fe, K, Mg, Ni, P, Pb, Sb, Si, Sn, Tl, and/or U
a=1
b=0.05 to 1.0
c=0 to 2

The numerical values of a, b, and c represent the relative gram-atom ratios of the elements Mo, X, and Y, respectively, which are present in the catalyst composition. The elements Mo, X, and Y are present in the catalyst composition in combination with oxygen.

Generally, the process of preparing the catalyst used in the patent includes forming a precursor solution of the compounds of the selected metals. This solutions is usually dried to obtain a solid which is broken up and calcined to form oxides. In Example 35, the precursor solution was filtered, allowed to stand three days, and then filtered again. The resulting filtrate was dried and processed to produce a catalyst. The catalyst was tested as a neat catalyst without a support.

None of the prior art has disclosed or suggested the surprising advantages of using a support for the filtrate. It is well known that catalyst performance can be reduced by the presence of a support as can be seen from Examples 36 and 37 of the patent. The same catalyst used with a support in Example 37 performed extremely poorly as compared to the neat catalyst used in Example 36.

SUMMARY OF THE INVENTION

The present invention relates to a process for the low temperature oxydehydrogenation of ethane to ethylene in a gas phase using a supported catalyst, wherein the supported catalyst is produced by the steps comprising preparing a precursor solution having soluble and insoluble portions of compounds of metals to form part of the catalyst, separating the soluble portion of the precursor portion, impregnating a catalyst support with the soluble portion of the precursor solution, and thereafter, activating the impregnated support to produce the supported catalyst.

The insolubles can be removed using well known methods such as filtering through sintered glass, and filtering through filter paper with or without suction. In addition, centrifuging can be used or the insolubles can be allowed to settle to the bottom of the precursor solution and the soluble portion decanted.

For commercial use of low temperature oxydehydrogenation of ethane to ethylene, it is advantageous to use a supported catalyst rather than a neat catalyst because the support spreads the incoming gas stream throughout the reaction zone, distributes heat, and minimizes loss of pressure while allowing a continuous flow of the gas stream.

Supported catalysts in the prior art are produced by impregnating a support with a precursor solution containing both soluble and insoluble portions and thereafter, are activated. It has been found that the insoluble portion tends to remain in the outer surface of the support.

The outer layer of insolubles becomes a catalyst as a result of the activating step and can cause several problems. The outer layer of catalyst can clog many pores so that the supported catalyst does not operate efficiently during the process due to gas paths being eliminated. In addition, some of the catalytic particles on the surface of the support can be carried along the stream to other parts of the system and thereby cause clogging and/or local hot spots.

It is known in the art that the use of a support for a catalyst can introduce undersirable ions. There are known pretreatments for supports used to minimize the presence of undesirable ions on the supports. Such pretreatments are used prior to impregnating such as washing the support with nitric acid. The suitability of pretreatments is determined empirically in the art.

DISCUSSION OF THE INVENTION

Generally, a broad range of supported catalysts are within the scope of the invention. The preferred supported catalysts are oxides of compositions containing Mo, V, and Nb. These preferred catalysts include the catalysts disclosed in the aforementioned U.S. Pat. No. 4,250,346 and catalysts disclosed in U.S. Pat. No. 4,524,236 and co-pending application Ser. No. 625,778, filed June 28, 1984 as calcined catalysts having the composition

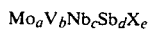
$Mo_aV_bNb_cSb_dX_e$

X = nothing or at least one of the following : Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn, and W; and a = 0.5 to 0.9
b = 0.1 to 0.4
c = 0.001 to 0.2
d = 0.001 to 0.1
e = 0.001 to 1.0

The values of a, b, c, d, and e constitute relative gram-atoms of the elements Mo, V, Nb, Sb, and X, respectively. The elements are present in combination with oxygen in a form of various oxides.

Preferably, the precursor solution for the catalyst is prepared from a solution of soluble compounds and/or complexes and/or compounds of each of the metals. The precursor solution is preferably an aqueous system having a pH of 1 to 12 and more preferably a pH of 5±3, at a temperature of from about 20° C. to about 100° C.

Generally, a mixture of compounds containing the elements is prepared by dissolving sufficient quantities of soluble compounds and dispersing the insoluble compounds so as to provide a desired gram-atom ratios of the elements in the precursor solution.

There are three parameters which should be determined before the catalyst support is impregnated. One parameter is the quantity of liquid which the support can absorb so that the quantity of the precursor solution can be adjusted accordingly. The amount of liquid which the support can absorb can be determined empirically. Another parameter is the amount of catalyst in the support for achieving optimum performance of the supported catalyst. This can be determined empirically. Generally, the loading or amount of catalyst should be from about 25% to about 35% of the weight of the supported catalyst. The other parameter is the composition of the precursor solution it can be determined empirically as to the amounts of the compounds of the elements necessary in the precursor solution in order to obtain a soluble portion to result in a predetermined weight of the catalyst.

The precursor solution is prepared so that the weight of the soluble portion is in accordance with the amount desired and the volume of liquid is appropriate for the support. Usually, the precursor solution is prepared with an excess of liquid and then the liquid is removed by heating the precursor solution.

After the precursor solution is impregnated into the support, the wet support is dried rapidly. It is convenient to carry out the impregnation in a heated container. The dried impregnated support is calcined by heating to a temperature from about 220° C. to about 550° C. in air or oxygen for a period of time from about one minute to about 24 hours to produce the desired supported catalyst composition. Generally, the higher the temperature the shorter the period of time required.

A drying at about 120° C. for about 16 hours removes most of the residual water and about one third of the ammonia from the impregnated support.

The activating step can be carried out immediately after drying step or delayed many months without adverse results. Generally, the activation is carried out by heating the impregnated support to about 350° C. and maintaining this temperature for about 6 hours. The time can be varied from several hours to 24 hours or more. The heating step is preferably carried out without any interruptions. The temperature can also be varied. The flow of air for optimizing the supported catalyst can be determined empiricably.

Suitable supports for the catalyst include silica, aluminum oxide, silicon carbide, zirconia, titania, and mixtures thereof.

A support having relatively low surface area, less than about 1.0 square meter per gram, and relatively large pores, medium pore diameter greater than about 10 microns. Table 1 shows a variety of supports commercially available and generally suitable for the invention. Table 1 includes available published data on the support.

TABLE I

| SUPPORT | COMPOSITION (%) | | | SIZE (IN) | SHAPE | SURFACE AREA M²/g | PORE VOLUME CC |
|---|---|---|---|---|---|---|---|
| | Al₂O₃ | SiO₂ | Others | | | | |
| 1 | 89.4 | 9.3 | | ¼ | PELLETS | .81–.87 | .21–.29 |
| 2 | 99.6 | | | 3/16 | PELLETS | .7–1.3 | .25–.34 |
| 3 | 99.6 | | | ¼ | RINGS | .7–1.3 | .25–.34 |
| 4 | 86.9 | 11.6 | | ¼ | PELLETS | .02–.08 | .17–.25 |
| 5 | 86.1 | 11.8 | | ¼ | SPHERES | 0.0095 | .18–.26 |
| 6 | 86.1 | 11.8 | | ¼ | SPHERES | .005–.95 | .18–.26 |
| 7 | 87.0 | 11.4 | | ⅛ | PELLETS | 0.0450 | .28 |
| 8 | 87.0 | 11.4 | | ⅛ | PELLETS | 0.0640 | 0.290 |
| 9 | 85.5 | 12.6 | | 3/16 | SPHERES | 0.0640 | .21–.27 |
| 10 | 86.1 | 12.0 | | ¼ | SPHERES | .005–.04 | .15–.25 |
| 11 | | | (b) | 5/16 | RINGS | .34 | .550 |
| 12 | 86.2 | 12.4 | | 5/16 | RINGS | 0.1720 | 0.464 |
| 13 | ZrO₂ | CaO | | ¼ | SPHERES | 0.1020 | 0.155 |
| 14 | | 100.0 | | | POWDER | 3.0 | |
| 15 | | | (c) | 5/16 | RINGS | 0.0890 | 0.390 |
| 16 | | 100.0 | | | POWDER | 1–3.5 | |

APPARENT     PORE SIZE DISTRIBUTION     APPARENT     LEACHABLE (a)

TABLE I-continued

| SUPPORT | DENSITY g/CC | 10% MICRONS | 50% MICRONS | 90% MICRONS | POROSITY % | Na | K | Ca | Mg |
|---|---|---|---|---|---|---|---|---|---|
| 1 | | 120.00 | 29.0 | 9.0 | 45–50 | | | | |
| 2 | | 190.00 | 1.2 | 8.5 | 50–56 | | | | |
| 3 | | 3.00 | 1.2 | 8.5 | 50–56 | | | | |
| 4 | | | 18.0 | 6.0 | 39–45 | | | | |
| 5 | | 350.00 | 130.0 | 45.0 | 49–55 | 7.8 | 2 | 2.0 | 4 |
| 6 | | | 130.0 | 45.0 | 49–55 | | | | |
| 7 | 3.22 | 73.00 | 26.0 | 8.0 | 47–54 | 9.0 | 2 | 0.5 | 2 |
| 8 | 3.00 | 157.00 | 29.0 | 9.0 | 50.7 | 9.0 | 3 | 2.0 | 1 |
| 9 | 3.85 | 65.00 | 35.0 | 9.0 | 46–52 | | | | |
| 10 | | 190.00 | 75.0 | 35.0 | 37–42 | | | | |
| 11 | 2.6 | 90.0 | 23.0 | 2.0 | | | | | |
| 12 | | 130.00 | 21.0 | 2.6 | 59.4 | 8.0 | 5 | 1.0 | 2 |
| 13 | 3.15 | 295.00 | 32.0 | 6.0 | 43.9 | | | | |
| 14 | | | 0.7 | | | | | | |
| 15 | | 86.0 | 22.0 | 7.0 | 58.3 | | | | |
| 16 | | | 7.0 | | | 0.8 | 2125 | 129 | 21 (d) |

(a) Norton Co. C.P.T.D. Test Method No. 63-78, "Determination of Nitric Acid Soluble Na, K, Ca, and Mg in Alumina Catalyst Carriers."
(b) Alumina with clay binder
(c) Silica fused with glass, crushed to size
(d) Other leachables ppm: Al-182, Fe-40; P-56; Si-104; B-184; Mo-325.

Preferably, the molybdenum is introduced into the solution in the form of ammonium salts such as ammonium paramolybdate, or organic acid salts of molybdenum such as acetates, oxalates, mandelates, and glycolates. Some other partially water soluble molybdenum compound which may be used include molybdenum oxides, molybdic acid, and chlorides of molybdenum.

Preferably, the vanadium is introduced into the solution in the form of ammonium salts such as ammonium meta-vanadate and ammonium decavanadate, or organic acid salts of vanadium such as acetates, oxalates, and tartrates. Partially water soluble vanadium compounds such as vanadium oxides, and sulfates of vanadium can be used.

Preferably, the niobium and tantalum, when used, are in the form of oxalates. Other sources of these metals in soluble form include compounds in which the metal is coordinated, bonded or complexed to a beta-diketonate, carboxylic acid, and amine, and alcohol, or an alkanolamine.

Preferably, the antimony is introduced into solution in the form of antimony oxalate. Other soluble and insoluble compounds of antimony can be used such as antimony oxide and antimony chloride.

The X component of the catalyst can be soluble or insoluble compounds, preferably soluble. Compounds which are strongly reducing may adversely reduce the oxidation states of the metals.

The following are some preferable compounds for the X components. One is titaniun in the form of a water soluble chelate coordinated with ammonium lactate, and others are titanium compounds in which the metal is coordinated, or complexed to a beta-diketonate, a carboxylic acid, an amine, an alcohol or an alkanolamine. Generally, nitrates are desirable along with water soluble chlorides and organic acid salts such as acetates, oxalates, tartrates, lactates, salicylates, formates, and carbonates. Preferred compounds for tungsten are in the form of ammonium salts such as ammonium paratungstate or other water soluble compounds such as tungstic acids.

Preferably, the supported catalyst is prepared by the following general procedure. The vanadium compound is mixed with water to form a first solution or suspension, the niobium, and antimony, are mixed with water to form a second solution or suspension, and molybdenum compound is mixed with water to form a third solution or suspension. Any X compounds which are ammonium salts are mixed with the first solution. Otherwise, X compounds are mixed into the second solution. The first and second solutions are heated separately and mixed for about fifteen minutes; and then combined and mixed with heating for about fifteen minutes. The third solution is heated and mixed, and then added to the combined first and second solutions to form a precursor solution. After mixing and heating of the precursor solution for about fifteen minutes, the precursor solution is ready for the next step, filtering.

It has been found that it is not good to filter the hot precursor solution because a poor supported catalyst is produced from the filtrate. It is convenient and simple to allow the precursor to cool to room temperature and remain undisturbed for a few days and merely decant the solution.

The filtrate is used to impregnate the support. The support is dried rapidly in air usually, but the drying could be carried out in an inert atmosphere. The filtering can be carried out using sintered glass, or a paper filter with or without suction.

It has been found that catalyst surface area and activity depend on the digestion time, i.e., the time taken to evaporate the combined solution to dryness. Compositions allowed to digest for relatively long periods of time, thirty minutes or more, before drying at 120° C. generally undergo particle growth with loss in surface area.

It is believed that the catalyst for the invention should have one or more of the metal components slightly below their highest possible oxidation states. The calcining is carried out with the flow of air or some other oxygen containing gas over the dry solids prepared from the solutions to control the reducing actions of reducing agents such as $NH_3$ or organic reducing agents which are introduced into the solution system from which the catalysts are prepared. The rate of flow of the gas can be determined experimentally for the apparatus and the quantities of solids being used for optimizing the properties of the catalyst being produced.

One or more of the free valances of metals in the catalyst are occupied by one or more of oxide, hydroxyl, and $CO_3$.

The raw material used as the source of the ethane can be a gas stream which contains at least three volume percent of ethane. The gas stream can also contain minor amounts of hydrogen, carbon monoxide, and the $C_3$-$C_4$ alkanes and alkenes, less than five volume percent of each. The gas stream can also contain major amounts, more than five volume percent, of nitrogen, methane, carbon dioxide, and water in the form of steam.

The catalyst of the invention is substantially limited to the oxydehydrogenation of ethane to ethylene because the catalyst does not efficiently oxydehydrogenate propane, n-butane, and butene-1, but predominantly burns these gases to carbon dioxide and other oxidized carbonaceous products.

The reaction mixture is carrying out the process is generally one mol of ethane, 0.01 to 1.0 mol of molecular oxygen either as pure oxygen or in the form of air, and zero to 4.0 mol of water in the form of steam. The water or steam is used as a reaction diluent and as a heat moderator for the reaction. Other gases may be used as reaction diluent or heat moderators such as nitrogen, helium, carbon dioxide, and methane.

During the course of the reaction, one mol of water is formed for each mol of ethane that is oxydehydrogenated. The water from the reaction results in the formation of some acetic acid. Under several atmospheres of pressure, about 0.05 to 0.25 mol of acetic acid per mol of ethylene is formed.

The water that is added to the feed stream will also cause the formation of additional amounts of acetic acid, up to about 0.25 to 1.0 mol of acetic acid per mol of ethylene that is formed.

The gaseous components of the reaction mixture include ethane and oxygen, and possibly a diluent, and these components are uniformly admixed prior to being introduced into the reaction zone. The components may be preheated, individually or after being admixed, prior to being introduced into the reaction zone which should have temperature of from about 200° C. to about 450° C.

The reaction zone generally has a pressure of from about 1 to 30 atmospheres and preferably 1 to 20 atmospheres; a temperature of from about 150° C. about to 450° C., and preferably from about 200° C. to about 400° C.; a contact time between the reaction mixture and the catalyst of from about 0.1 to about 100, and preferably from about 1 to 10 seconds; and a space velocity of from about 50 to 5000h$^{-1}$, and preferably 200 to 3000h$^{-1}$.

The contact time is defined as the ratio between the apparent volume of the catalyst bed and the volume of the gaseous reaction mixture feed to the the catalyst bed under the given reaction conditions in a unit of time.

The space velocity is calculated by determining total reactor outlet gas equivalent in liters of the total effluent evolved over a period of one hour divided by the liters of catalyst in the reactor. This room temperature volume is converted to the volume at 0° C. at 760 mm Hg:

$$\text{space velocity} = \frac{\text{liters of outlet gas equivalents per hour}}{\text{liters of catalyst in reactor}} = h^{-1}$$

The reaction pressure is initially provided by the feed of the gaseous reactant and diluent and after the reaction has commenced, the pressure is maintained, preferably, by the use of suitable back-pressure controllers placed on the reactor outlet stream.

The reaction temperature is preferably provided by placing the catalyst bed within a tubular converter having walls immersed in a suitable heat transfer medium such as tetralin, molten salt mixtures, or other suitable heat transfer agents heated to the desired reaction temperature.

Generally, the process can be carried out in a single stage with all of the oxygen for the reaction being supplied along with an inert diluent. It is desirable to operate without a diluent to facilitate the isolation of the ethylene produced. When a diluent is not used this presents several problems because a large amount of oxygen can create a hazardous condition and the uncontrolled presence of water and acetic acid can adversely affect the production of ethylene. Accordingly, it is believed that the use of multiple stages improves the process. Multiple stages allows the oxygen needed for the total reaction of the ethane to be introduced at various stages and thereby avoid a potentially hazardous condition.

Surprisingly, the supply of oxygen in various stages rather than a supply of the total amount of the oxygen in the initial stage has no detrimental affect on the production of ethylene. In addition, the use of stages enables the control of the amount of water present in stages subsequent to the first stage. If desired, water can be withdrawn and thereby minimize the formation of acetic acid.

It is desirable to compare the performance of the instant catalysts with prior art catalysts. Optimally, a comparison should be made for the same set of conditions and the same equipment. This is not always convenient or economically justified.

A reasonably good basis for comparing catalyst performance can be achieved by comparing selectivity to ethylene for the same conversion of ethane. This can be accomplished easily by taking advantage of the discovered substantially linear relationship between selectivity to ethylene and conversion of ethane over the useable operating temperature range. Thus, it is unnecessary to actually operate at the conversion of ethane being used for a comparison because one can interpolate or extropolate to any desired set of values from two sets of data.

EXAMPLES

Several examples were carried out to demonstrate the invention and compare it to the prior art.

The process for the various catalysts were carried out in a tubular reactor under the following conditions:

Gas feed composition was 8% by volume ethane, 6.5% by volume oxygen, and 85.5% by volume helium. The space velocity was about 720 h$^{-1}$ at a one atmosphere total pressure. The reactor consisted of a 14 millimeter diameter stainless steel straight tube heated in an oven with a blower and at a temperature of from 330° C. to 425° C. The reactor contained 25 grams of the catalyst. The reactor bed depth was about 14.0 centimeters so that the depth to cross section ratio was about ten. The liquid products, water and traces of acetic acid, were condensed in a trap and the gaseous products were analyzed for oxygen and carbon monoxide at 65° C. on a 3 m×3 mm column of 5 A molecular sieve (60/80 mesh). An analysis at 65° C. was carried out for carbon dioxide, ethylene, and ethane on a 1.8 m×3 mm column of material sold under the trademark POROPAK Q (50/80 mesh). In all cases, the conversion and selectivity calculations were based on the Stoichiometry:

$$C_2H_6 + \tfrac{1}{2}O_2 \rightarrow C_2H_4 + H_2O$$

$$C_2H_6 + 5/2 O_2 \rightarrow 2CO + 3H_2O$$

$$C_2H_6 + 7/2 O_2 \rightarrow 2CO_2 + 3H_2O$$

EXAMPLES 1 TO 8

A supported catalyst was prepared to have the following composition in the precursor solution for Examples 1 to 8:

$$Mo_{0.61}V_{0.25}Nb_{0.07}Sb_{0.037}Ca_{0.037}$$

Ammonium metavanadate in the amount of 9.90 grams (0.085 gram atom of V) was added to 100 ml of water and heated to 70° C. with stirring for fifteen minutes. Niobium oxalate amounting to 31.1 grams of solution containing 10% by weight calculated as $Nb_2O_5$ (0.0234 gram atom of Nb), antimony (III) oxalate amounting to 3.12 grams (0.0123 gram-atom of Sb) and calcium nitrate tetrahydrate amounting to 2.92 grams (0.0124 gram-atom of Ca) were added to a second 100 ml of water and heated to 70° C. with stirring for fifteen minutes. The second mixture was combined with the first mixture and the combination was heated at 70° C. with stirring for fifteen minutes. To a third 100 ml of water was added 35.3 grams (0.200 gram-atom of Mo) of ammonium paramolybdate. This mixture was heated to 70° C. with stirring for fifteen minutes and then added to the combined mixtures to form the precursor solution. The precursor solution was heated at 70° C. and stirred for fifteen minutes.

For the Examples 1 to 4, the precursor solution was filtered at 25° C. with wet filter paper. For the Examples 5 to 8, the precursor solution was filtered at 100° C. with wet filter paper using a steam-jacketed funnel.

A steam-heated stainless steel evaporating dish was used to reduce the liquid content in accordance with the absorbing properties of the support being used. The support was added to the disk while the heat was maintained and became impregnated. After about 15 minutes the support components not longer tended to adhere together. Additional drying of the impregnated support was carried out by heating to 120° C. for 16 hours with a continuous flow of air. This heating removes most of the residual water and about one-third of the ammonia present in the stirring materials.

The dried impregnated support was activated by heating to about 350° C. in an oven for about 5 hours with a flow of air through the oven. This resulted in the supported catalysts of the invention.

The supported catalysts were tested and the results of these tests are shown in Table II. Table II shows the support used and a detailed description of the supports can be found in Table I. Table II gives the selectivity for a 30% conversion to ethylene along with the conversion to ethylene at 400° C. These are good parameters for showing performance and indicate that the supported catalysts of the Examples 1 to 8 are good.

TABLE II

| Ex. | Support | Wt. % Loading | Selectivity at 30% Conversion | Conversion at 400° C. |
|---|---|---|---|---|
| 1 | 10 | 21.4 | 72.4 | 66.5 |
| 2 | 10 | 25.0 | 79.2 | 53.4 |
| 3 | 16 | 40.0 | 89.9 | 69.2 |
| 4 | 12 | 24.8 | 83.7 | 38.5 |
| 5 | 12 | 28.4 | 81.6 | 58.3 |
| 6 | 12 | 29.9 | 84.5 | 41.4 |
| 7 | 12 | 31.9 | 85.4 | 32.4 |
| 8 | 12 | 32.9 | 85.1 | 54.3 |

EXAMPLE 9

Using the procedure of Examples 1 to 8, two precursor solutions were prepared so that each precursor solution had the following composition:

$$Mo_{16}V_{6.8}Nb_{1.9}Sb_{1.0}Ca_{1.0}$$

One of the precursor solutions was evaporated to dryness in air with stirring in a stream-heated stainless steel evaporating dish. The resulting solid was broken and sieved to an 8×30 mesh and dried additionally in an oven at 120° C. for sixteen hours. The dried material was calcined in an oven equipped with a blower, at a temperature of 350° C. The temperature was raised from room temperature to 350° C. over a period of twenty minutes, and thereafter maintained at 350° C. for five hours. The resulting catalyst is identified therein at the "Feed Catalyst".

The other precursor solution was suction filtered at 100° C. The insoluble portion was made into a catalyst using the procedure carried out to prepare the Feed Catalyst. This catalyst is identified herein as the "Insoluble Catalyst". The soluble portion of this precursor solution was made into a supported catalyst using the procedure of Examples 1 to 8 and a support 10. Table III shows a comparison between the three catalyst of this Example.

TABLE III

| Catalyst | Composition | Wt. % of Feed | % Selectivity For 30% Conversion | % Conversion at 400° C. |
|---|---|---|---|---|
| Feed | $Mo_{16}V_{6.8}Nb_{1.9}Sb_{1.0}Ca_{1.0}$ | 100 | 78.4 | 48.1 |
| Insoluble | $Mo_{16}V_{18.5}Nb_{13.2}Sb_{3.4}Ca_{6.3}$ | 19.9 | 44 | 3.0 |
| Supported Soluble (29.9% loading) | $Mo_{16}V_{5.6}Nb_{0.5}Sb_{0.3}Ca_{0.3}$ | 80.1 | 83.6 | 38.8 |

EXAMPLES 10, 11 AND 12

The procedure of Examples 5 to 8 was used to make the supported catalysts as shown in Table IV using the support 12 in each Example. Table IV also shows the test results.

TABLE IV

| Ex. | Precursor Composition | % Loading | % Selectivity For 30% Conversion | % Conversion at 400° C. |
|---|---|---|---|---|
| 10 | $Mo_{16}V_{5.9}Nb_{0.37}Sb_{0.34}Ca_{0.45}$ | 29.9 | 80.2 | 55.8 |
| 11 | $Mo_{16}V_{5.24}Nb_{0.09}Sb_{0.37}Ca_{0.82}$ | 30.2 | 85.2 | 45.0 |
| 12 | $Mo_{16}V_{5.74}Nb_{0.12}Sb_{0.39}Ca_{0.11}$ | 30.2 | 85.8 | 54.8 |

We claim:

1. A process for preparing a supported catalyst of the low temperature oxydehydrogenation of ethane to ethylene in a gas phase, comprising the steps of: preparing a precursor solution having soluble and insoluble portions of compounds of metals to form part of the catalyst, separating the soluble portion of the precursor solution, impregnating a catalyst support with the soluble portion of the precursor solution, and thereafter, activating the impregnated support to produce the supported catalyst.

2. The process of claim 1, wherein the soluble portion is separated by filtering.

3. The process of claim 1, wherein the soluble portion is are separated by decanting.

4. The process of claim 1, wherein the catalyst is a calcined composition comprising Mo, V, and Nb.

5. The process of claim 1, wherein the catalyst is a calcined composition containing $$Mo_a V_b Nb_c Sb_d X_e$$

X = nothing or at least one of the following: Li, Sc, Na, Be, Mg, Ca, Sr, Ba, Ti, Zr, Hf, Y, Ta, Cr, Fe, Co, Ni, Ce, La, Zn, Cd, Hg, Al, Tl, Pb, As, Bi, Te, U, Mn, and W; and a = 0.5 to 0.9
b = 0.1 to 0.4
c = 0.001 to 0.2
d = 0.001 to 0.1
e = 0.001 to 1.0 for X equal to at least one element and e = 0 for X = 0;

The values of a, b, c, d, and e constitute relative gram-atoms.

UNITED STATES PATENT AND TRADEMARK OFFICE
CERTIFICATE OF CORRECTION

PATENT NO. : 4,596,787

DATED : June 24, 1986

INVENTOR(S) : R. M. Manyik et al.

It is certified that error appears in the above-identified patent and that said Letters Patent is hereby corrected as shown below:

Column 9, line 50, "stirring" should be -- starting --.

Signed and Sealed this

Seventeenth Day of October, 1989

Attest:

DONALD J. QUIGG

*Attesting Officer*     *Commissioner of Patents and Trademarks*